United States Patent [19]

Onizuka et al.

[11] Patent Number: 4,663,724
[45] Date of Patent: May 5, 1987

[54] METHOD FOR THE CONTINUOUS DETERMINATION OF THE CONCENTRATION OF A CARBONATE AND A SULFITE IN A LIQUID

[75] Inventors: Masakazu Onizuka; Naohiko Ukawa; Susumu Kono; Susumu Okino, all of Hiroshima, Japan

[73] Assignee: Mitsubishi Jukogyo Kabushiki Kaisha, Tokyo, Japan

[21] Appl. No.: 580,362

[22] Filed: Feb. 15, 1984

[30] Foreign Application Priority Data

Feb. 17, 1983 [JP] Japan .................. 58-23741

[51] Int. Cl.⁴ .................. G06F 15/46; G01N 35/08
[52] U.S. Cl. .................. 364/496; 73/53; 73/61 R; 364/497; 436/52; 436/133
[58] Field of Search .................. 364/496–500, 364/502, 550, 556; 73/23, 23.1, 53, 61 R, 61.1 R; 436/52, 122, 133

[56] References Cited

U.S. PATENT DOCUMENTS

| | | | |
|---|---|---|---|
| 3,437,446 | 4/1969 | Pierce | 436/122 X |
| 3,437,452 | 4/1969 | Bell et al. | 73/61 |
| 3,482,431 | 12/1969 | Mochizuki | 73/23 |
| 3,801,281 | 4/1974 | Thompson et al. | 436/133 X |
| 4,019,862 | 4/1977 | Dahms | 436/133 X |
| 4,251,503 | 2/1981 | Swindells et al. | 364/497 X |
| 4,397,957 | 8/1983 | Allison | 436/133 |
| 4,414,193 | 11/1983 | Fredette et al. | 364/500 |

FOREIGN PATENT DOCUMENTS 2135455  8/1984  United Kingdom .................. 436/133

OTHER PUBLICATIONS

Fundamentals of Analytical Chemistry, Douglas Skoog & D. M. West, 1963, (Holt, Rinehart & Winston; pub.), pp. 756–757.

Primary Examiner—Gary Chin
Assistant Examiner—Kevin J. Teska
Attorney, Agent, or Firm—Wenderoth, Lind & Ponack

[57] ABSTRACT

A solution or slurry containing a carbonate or sulfite, or both is continuously supplied into a tightly closed vessel, while any excess of the liquid is allowed to overflow the vessel. Sulfuric acid is supplied into the vessel to maintain the pH level of the liquid in the vessel at a value not exceeding 3. Air is supplied into the vessel as a carrier gas for $CO_2$ or $SO_2$ or both formed by the reaction of the carbonate or sulfite or both in the liquid with the sulfuric acid. The carrier gas is collected from the vessel, and the concentration of $CO_2$ or $SO_2$ or both in the carrier gas is determined. The concentration of the carbonate or sulfite or both in the liquid is obtained by calculations from the concentration of $CO_2$ or $SO_2$ or both, the flow rate of the liquid and the flow rate of the carrier gas.

1 Claim, 3 Drawing Figures

METHOD FOR THE CONTINUOUS DETERMINATION OF THE CONCENTRATION OF A CARBONATE AND A SULFITE IN A LIQUID

BACKGROUND OF THE INVENTION

1. Field of the Invention:

This invention relates to a method for the continuous determination of the concentration of a carbonate or sulfite, or both in a liquid, or more specifically in a solution or slurry.

2. Description of the Prior Art:

An absorbent slurry in an apparatus for liquid purification or desulfurization according to the wet lime process is a typical example of a liquid containing a carbonate and a sulfite. It is usual practice to control the desulfurizing capacity of such an apparatus by checking the pH level of a liquid being recirculated in an absorption tower and supplying an absorbent to keep the pH value of the liquid at a level which enables the apparatus to maintain its normal desulfurizing capacity.

The recent trend toward the saving of resources and energy has been calling for an improvement in the efficiency of a boiler or like apparatus forming a source of exhaust gas, and an increase in the speed at which its load is varied. This has given rise to the requirement for an apparatus for the desulfurization of such exhaust gas to be capable of working in harmony with any such change in the load of a boiler or like apparatus without lowering its desulfurizing capacity.

The pH control for the liquid in the absorption tower is hereinabove described, however, makes it difficult for the desulfurizing apparatus to maintain its satisfactory desulfurizing capacity for a prolonged period of time irrespective of a rapid change in the load of a boiler or like apparatus. This is due to the fact that the concentration of a carbonate and a sulfite in the absorbent slurry varies with a change in the load of desulfurization, even if the pH value of the liquid in the absorption tower may be controlled at a constant level. It is, therefore, essential to determine the concentration of a carbonate and a sulfite in the absorbent slurry in order to maintain the capacity of the desulfurizing apparatus at a satisfactory level irrespective of any such change in the load.

SUMMARY OF THE INVENTION

It is an object of this invention to provide a method which makes it possible to perform the continuous determination of the concentration of a carbonate or sulfite, or both in a solution or slurry rapidly and accurately.

A solution or slurry containing a carbonate or sulfite, or both is continuously supplied into a vessel shielded from the ambient air. Sulfuric acid is supplied into the vessel to maintain the pH level of the liquid in the vessel at a value not exceeding 3. Any excess of the liquid is allowed to overflow the vessel through a line having a liquidtight end. Air is supplied into the vessel as a carrier gas for $CO_2$ and $SO_2$ gases formed by the addition of the sulfuric acid. The carrier gas is released from the vessel, and the concentrations of $CO_2$ and $SO_2$ in the carrier gas are determined by a $CO_2$ concentration meter and a $SO_2$ concentration meter, respectively. The concentrations of the carbonate and sulfite in the liquid are obtained by calculations from the concentrations of $CO_2$ and $SO_2$, the flow rate of the liquid and the flow rate of the carrier gas.

DETAILED DESCRIPTION OF THE INVENTION

Figure 1:
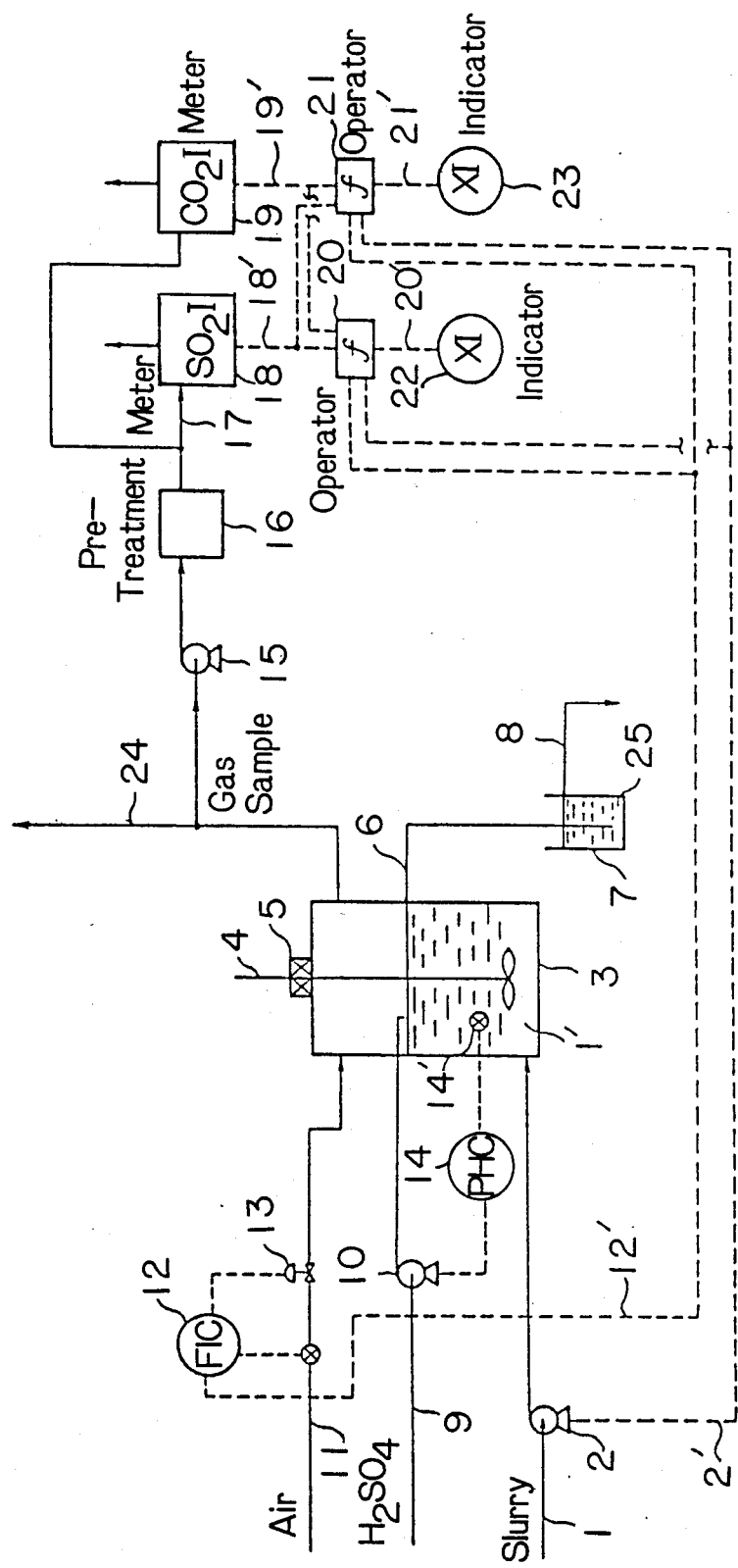
FIG. 1 is a diagram showing a method embodying this invention.

Referring to FIG. 1 of the drawings, there is shown a system which can be used for carrying out a method embodying this invention. A liquid 1 containing a carbonate or sulfite, or both is supplied into a tightly closed reaction vessel 3 through a metering pump 2. The pH level of the liquid 1' in the vessel 3 is detected by a pH sensor 14', while the liquid 1' is stirred by a stirrer 4 extending thriough gas seal 5. Sulfuric acid 9 is supplied into the vessel 3 through a micropump 10 so that the liquid 1' may maintain a pH value not exceeding 3. The operation of the micropump 10 is controlled by a pH controller 14. Any excess of the liquid 1' is allowed to flow from the vessel 3 to a waste liquid reservoir 7 through an overflow line 6 having a liquid-sealed end immersed in the liquid in the reservoir 7. The waste liquid 25 is discharged from the reservoir 7 through a line 8. The carbonate and sulfite in the liquid 1 react with the sulfuric acid supplied for the purpose of pH control and form stoichiometrically equal amounts of $CO_2$ and $SO_2$ and a sulfate, as shown by the following formulas:

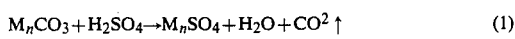

$$M_nCO_3 + H_2SO_4 \rightarrow M_nSO_4 + H_2O + CO_2 \uparrow \qquad (1)$$

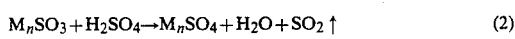

$$M_nSO_3 + H_2SO_4 \rightarrow M_nSO_4 + H_2O + SO_2 \uparrow \qquad (2)$$

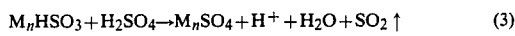

$$M_nHSO_3 + H_2SO_4 \rightarrow M_nSO_4 + H^+ + H_2O + SO_2 \uparrow \qquad (3)$$

where M stands for a metal, or the like.

The $CO_2$ and $SO_2$ are collected from the vessel 3 with air 11 supplied to the vessel 3 as a carrier gas through a flow rate controller 12 and a flow control valve 13. A part of the gas 24 thus collected is delivered by a gas pump 15 to a pretreating device 16 for dust and moisture removal. The pretreated gas 17 is delivered to a $CO_2$ concentration meter 19 and a $SO_2$ concentration meter 18, whereby the concentrations of $CO_2$ and $SO_2$ in the gas 17 are determined. A signal 19' representing the concentration of $CO_2$, a signal 18' representing the concentration of $SO_2$, a signal 12' representing the flow rate of the air used as a carrier gas and a signal 2' representing the flow rate of the liquid 1 are transmitted to operators 21 and 20, whereby the concentrations of the carbonate and sulfite in the liquid 1 are obtained by calculations. A signal 21' representing the concentration of the carbonate and a signal 20' representing the concentration of the sulfite are transmitted to indicators 23 and 22, respectively.

The invention will now be described more specifically by way of example.

EXAMPLE

The method of this invention was carried out by employing the system of FIG. 1. A slurry containing 0.5 mol of gypsum, 10 m mols of calcium carbonate and 10 m mols of calcium sulfite, all per liter, was supplied by a metering pump 2 into the vessel 3 at a rate of 100 ml/min. Any liquid 1' in excess of 500 ml was removed from the vessel 3 through the overflow line 6. The pH value of the liquid 1' in the vessel 3 was detected by the pH sensor 14' composed of the electrode. An aqueous solution containing 0.5 mol of sulfuric acid per liter was supplied into the vessel 3 by the micropump 10 whenever the pH level of the liquid 1' exceeded the value of 3 set on the pH controller 14. The stirrer 4 was kept in service throughout the period of the analysis. Air was supplied at a rate of 5N liters per minute as a carrier gas for the resulting $CO_2$ and $SO_2$. A part of the gas 24 leaving the vessel 3 was pretreated for dust and moisture removal, and delivered to the concentrations meters 18 and 19 for $SO_2$ and $CO_2$ determination. The resulting signals 18' and 19', and the signals 2' and 12' representing the flow rates of the liquid and the carrier gas, respectively, were transmitted to the operators 20 and 21. The following calculations were made therein to determine the concentrations of the carbonate and sulfite in the liquid:

$$\text{Concentration of the carbonate}(m \text{ mols/lit.}) = \frac{F_1 \times 10^6}{(10^6 - X_1 - X_2)} \times \frac{X_1}{22.4} \times \frac{10^3}{F_2} \quad (4)$$

$$\text{Concentration of the sulfite}(m \text{ mols/lit.}) = \frac{F_1 \times 10^6}{(10^6 - X_1 - X_2)} \times \frac{X_2}{22.4} \times \frac{10^3}{F_2} \quad (5)$$

where $X_1$ is the concentration of $CO_2$ (ppm), $X_2$ is the concentration of $SO_2$ (ppm), $F_1$ is the flow rate of air (N lit./min.) and $F_2$ is the flow rate of the liquid (lit./min.).

Figure 2:
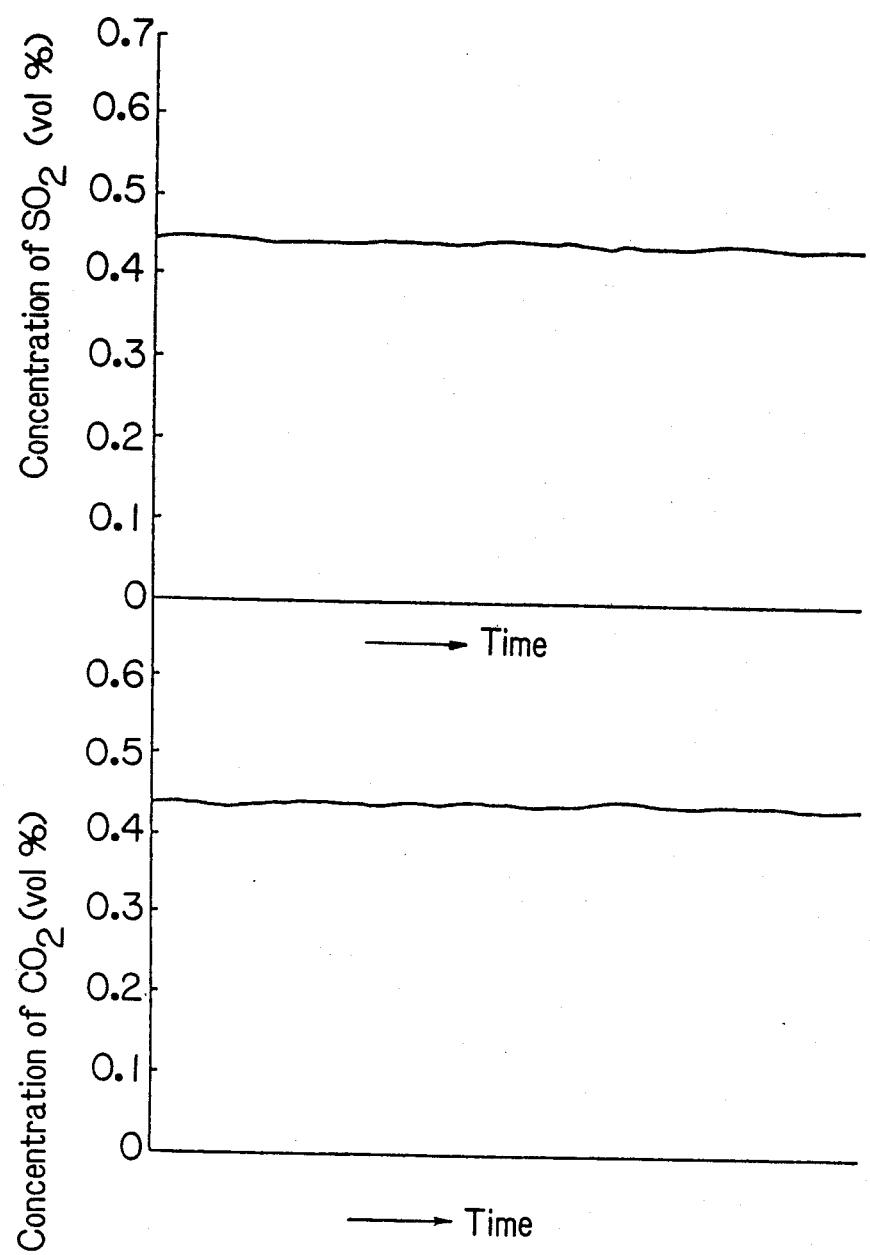
FIG. 2 is a graph showing by way of example the results obtained by carrying out the method of this invention.
Figure 3:
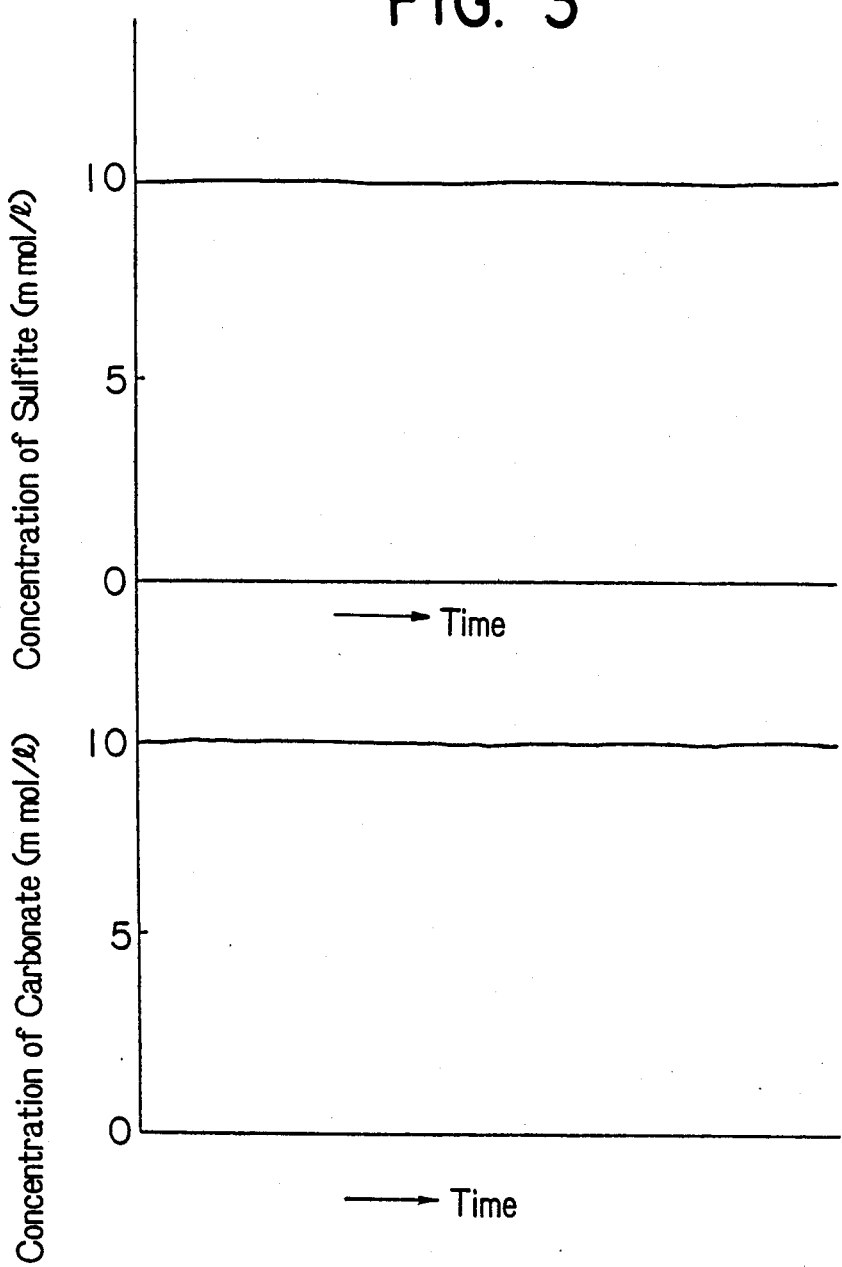
FIG. 3 is also a graph showing by way of example the results obtained by carrying out the method of this invention.

The concentrations of $CO_2$ and $SO_2$ in the gas leaving the vessel 3 are shown in FIG. 2, while the concentrations of the carbonate and sulfite determined by the calculations based on the results of FIG. 2 are shown in FIG. 3.

What is claimed is:

1. A method for the continuous determination of the concentration of a carbonate or sulfite, or both in a slurry, comprising:

supplying a slurry containing a carbonate or sulfite, or both continuously into a vessel shielded from ambient air, while allowing any excess of said slurry to overflow said vessel;

supplying sulfuric acid into said vessel to maintain the pH level of said slurry in said vessel at a valve not exceeding 3;

supplying said vessel with air as a carrier gas for $CO_2$ or $SO_2$ or both formed by the reaction of said carbonate or sulfite or both with said sulfuric acid;

collecting said carrier gas from said vessel;

determining the concentration of said $CO_2$ or $SO_2$ or both in said carrier gas; and calculating the concentration of said carbonate or sulfite or both in said slurry from said concentration of said $CO_2$ or $SO_2$ or both, the flow rate of said slurry and the flow rate of said carrier gas, on the basis of the following formulae:

$$\text{Concentration of said carbonate in } m \text{ mols liter} = \frac{F_1 \times 10^6}{(10^6 - X_1 - X_2)} \times \frac{X_1}{22.4} \times \frac{10^3}{F_2}$$

$$\text{Concentration of said sulfite in } m \text{ mols/liter} = \frac{F_1 \times 10^6}{(10^6 - X_1 - X_2)} \times \frac{X_2}{22.4} \times \frac{10^3}{F_2}$$

where $X_1$ is the concentration of $CO_2$ in ppm, $X_2$ is the concentration of $SO_2$ in ppm, $F_1$ is the flow rate of said carrier gas in liters/minute, and $F_2$ is the flow rate of said slurry in liters/minute.

* * * * *